United States Patent [19]
Aoki et al.

[11] 3,931,219

[45] Jan. 6, 1976

[54] PROCESS FOR PREPARING HEXAHYDROTHIENO[3,4-D]IMIDAZOLE-2,4-DIONES

[75] Inventors: Yasuhiko Aoki, Toyonaka; Hiroyuki Suzuki; Hisao Akiyama, both of Nishinomiya; Shigeru Okano, Kawanishi, all of Japan

[73] Assignee: Sumitomo Chemical Company, Limited, Japan

[22] Filed: Sept. 27, 1974

[21] Appl. No.: 509,904

[30] Foreign Application Priority Data

Sept. 27, 1973 Japan.............................. 48-109021

[52] U.S. Cl. ............................................ 260/309.7
[51] Int. Cl.$^2$ ........................................ C07D 49/34
[58] Field of Search .............................. 260/309.7

[56] References Cited
UNITED STATES PATENTS

| | | | |
|---|---|---|---|
| 2,489,232 | 11/1949 | Goldberg et al. | 260/309.7 |
| 2,489,234 | 11/1949 | Goldberg et al. | 260/309.7 |
| 2,519,720 | 8/1950 | Surmatis et al. | 260/309.7 |
| 3,700,659 | 10/1972 | Gerecke et al. | 260/309.7 X |
| 3,876,656 | 4/1975 | Aoki et al. | 260/309.7 |

FOREIGN PATENTS OR APPLICATIONS 7,037,776 11/1970 Japan.............................. 260/309.7

OTHER PUBLICATIONS

Gerecke et al., Helv. Chim. Acta, Vol. 53, Fasc. 5 (1970)–Nr. 116, pp. 991–999.

*Primary Examiner*—Ethel G. Love
*Attorney, Agent, or Firm*—Stewart and Kolasch, Ltd.

[57] ABSTRACT

In the conversion of a hexahydrofuro[3,4-d]-imidazole-2,4-dione compound into the corresponding hexahydrothieno[3,4-d]imidazole-2,4-dione compound, an improved process which comprises reacting the starting hexahydrofuro[3,4-d]imidazole-2,4-dione compound with a dithiocarbamate.

9 Claims, No Drawings

PROCESS FOR PREPARING HEXAHYDROTHIENO[3,4-D]IMIDAZOLE-2,4-DIONES

The present invention relates to a process for preparing hexahydrothieno[3,4-d]imidazole-2,4-diones. More particularly, it relates to an industrially advantageous process for conversion of hexahydrofuro[3,4-d]imidazole-2,4-diones into the corresponding hexahydrothieno[3,4-d]imidazole-2,4-diones.

Although the process for this invention is generally applicable to the conversion of any compound having a hexahydrofuro[3,4-d]imidazole-2,4-dione structure into the corresponding compound having a hexahydrothieno[3,4-d]imidazole-2,4-dione structure, it will be hereinafter illustrated on the following conversion as an example for convenience:

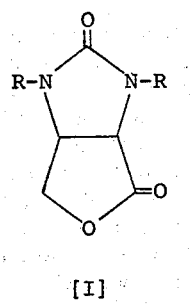

[I]

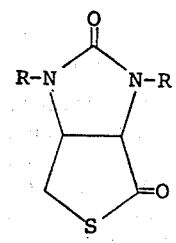

[II]

wherein R is alkyl, aryl or aralkyl.

In the above significances, the alkyl group may be those having preferably not more than 8 carbon atoms (e.g. methyl, ethyl, propyl, butyl). The aryl group includes those having not more than 10 carbon atoms (e.g. phenyl, tolyl, xylyl, naphthyl). As the aralkyl group, there may be included those having not more than 18 carbon atoms (e.g. benzyl, phenethyl, naphthylmethyl).

The thiolactones [II] are valuable intermediates in the synthesis of various pharmaceuticals such as biotin, α-dehydrobiotin and trimethaphan camphorsulfonate.

For preparation of the thiolactones [II] from the corresponding lactones [I], there are known two processes, i.e. the one as described in M. Gerecke et al.: Helvetica Chimica Acta, 53, 991–999 (1970) (hereinafter referred to as "Process A") and the one as described in Japanese Patent Publication (unexamined) No. 42793/72 (hereinafter referred to as "Process B").

In Process A, the starting lactone [I] is heated with potassium thioacetate in dimethylformamide or dimethylacetamide at a temperature higher than about 150°C to give the objective thiolactone [II]. By this process, the crude product is obtainable in a high yield. Since, however, such a high temperature as about 150°C or more causes the decomposition of the reagent potassium thioacetate and the once produced thiolactone [II], the purity of the product is considerably lowered. Particularly when the starting lactone [I] is optically active, the optical purity of the produced thiolactone [II] is markedly reduced. In addition, it is industrially disadvantageous to use such an expensive reagent as potassium thioacetate.

In Process B, the starting lactone [I] is heated with an alkali metal hydrosulfide in a polar solvent such as dimethylacetamide at about 120°C to give the objective thiolactone [II]. In order to increase the yield of the product, however, it is necessary to saturate the reaction system with hydrogen sulfide at such a high temperature as about 120°C. For industrial realization of this condition, an expensive reactor such as a glass-lined autoclave is needed. In addition, the yield of the product is about 76% at the best and is still not satisfactory.

As the result of an extensive study, it has now been found that the lactone [I] can be converted into the corresponding thiolactone [II] in an excellent yield with a high purity without any disadvantage as seen in the said conventional processes by the use of a dithiocarbamate as a sulfurizing agent. The present invention is based on this finding.

According to the present invention, the lactone [I] is reacted substantially with a dithiocarbamate to give the corresponding thiolactone [II].

As the dithiocarbamate, there may be used the one of the formula: R'NHCSSM wherein R' is alkyl (preferably having not more than 8 carbon atoms), cycloalkyl (preferably having 5 or 6 carbon atoms) or aryl (preferably having not more than 12 carbon atoms) and M is an alkali metal, which can be prepared by a conventional procedure, for instance, by reacting an alkali metal hydrosulfide (e.g. sodium hydrosulfide, potassium hydrosulfide) with an isothiocyanate such as an alkyl isothiocyanate (e.g. ethyl isothiocyanate, n-butyl isothiocyanate), a cycloalkyl isothiocyanate (e.g. cyclopentyl isothiocyanate, cyclohexyl isothiocyanate) or an aryl isothiocyanate (e.g. phenyl isothiocyanate), or reacting a primary amine with carbon disulfide and an alkali metal hydroxide.

In case of using sodium hydrosulfide as the starting material, for instance, an isothiocyanate is added to a suspension of sodium hydrosulfide in a high boiling point polar solvent (e.g. sulfolane, N,N-dimethylformamide, N,N-dimethylacetamide, tetramethylurea, hexamethylphosphoramide), and the resultant mixture is subjected to dehydration by the use of a dehydrating agent (e.g. anhydrous sodium sulfate, anhydrous magnesium sulfate, molecular sieves) to give the dithiocarbamate. Instead of using the dehydrating agent, dehydration may be performed by azeotropic elimination of water in the presence of an appropriate solvent (e.g. benzene, toluene).

In case of using potassium hydrosulfide, for instance, potassium hydroxide is dissolved in the said high boiling point polar solvent or its mixture with an alcohol (e.g. methanol, ethanol), the resulting solution is saturated with hydrogen sulfide and, when the alcohol is employed, the resultant saturated solution is distilled under reduced pressure to eliminate the same. To the resulting solution or suspension of potassium hydrosulfide, an isothiocyanate is added, and the resultant mixture is stirred at room temperature for 1 to 2 hours, followed by dehydration in the same manner as above to give the dithiocarbamate.

The thus produced dithiocarbamate may be used in the reaction with the lactone [I] with or without previous separation from the reaction mixture containing the same.

The reaction between the lactone [I] and the dithiocarbamate is usually effected in a high boiling point polar solvent (e.g. sulfolane, N,N-dimethylformamide, N,N-dimethylacetamide, tetramethylurea, hexamethylphosphoramide) by heating at a temperature of about 100° to 120°C for about 4 to 6 hours.

After the reaction is completed, a dilute mineral acid (e.g. hydrochloric acid, sulfuric acid) may be added dropwise to the reaction mixture while cooling with ice. The resultant mixture is extracted with an organic solvent (e.g. benzene, toluene) the organic extract is washed with water and the washed solution is concentrated under reduced pressure. The residue is treated with an appropriate solvent (e.g. ether, hexane, aqueous methanol, aqueous ethanol) or recrystallized from any appropriate solvent (e.g. aqueous methanol, aqueous ethanol, aqueous acetone) to give the objective thiolactone [II] as crystals.

Alternatively, the said residue may be dissolved in an appropriate solvent (e.g. benzene, toluene) or, after acidifying with a dilute mineral acid, extracted with an appropriate solvent (e.g. benzene), and the resulting solution is treated with the combination of a dilute mineral acid and tin, zinc or iron at a temperature of room temperature to 70°C, preferably of about 60° to 65°C to give the thiolactone [II] of high purity.

As stated above, the process of this invention can advantageously afford the thiolactone [II] in an quantitative yield with a extremely high purity. It is particularly notable that the thiolactone [II] of high optical purity is obtainable by the use of the lactone [I] which is optically active. Accordingly, for instance, this invention can provide an extremely important and valuable, optically active intermediate for the synthesis of the optically active biotin, i.e. d-biotin.

Practical and presently preferred embodiments of this invention are illustratively shown in the following Examples.

EXAMPLE 1 cis-1,3-Dibenzylhexahydrofuro[3,4-d]imidazole-2,4-dione ($[\alpha]_D^{20}$ + 61.5° (C = 2 in CHCl$_3$)) (10.0 g) is added to a solution of sodium n-butyldithiocarbamate (16.0 g) in sulfolane (120 ml), and the mixture is heated with stirring at 110°C for 6 hours. The reaction mixture is acidified by the addition of 12% hydrochloric acid (200 ml), and the reaction product is extracted with benzene (160 ml). The benzene extract is washed with water, followed by the addition of 7% hydrochloric acid (120 ml) and zinc powder (10.0 g) thereto. The mixture is heated at 60° to 65°C for 2 hours while stirring. The reaction mixture is cooled to room temperature and filtered, and the filtrate is separated. The organic layer is washed with water and concentrated in vacuo to give the residual oil (12.1 g). The residual oil is triturated with 90 v/v % methanol (40 ml), and the precipitate is collected by filtration to give cis-1,3-dibenzylhexahydrothieno[3,4-d]imidazole-2,4-dione (8.90 g). Yield, 85.0%. M.P. 122° to 123°C. $[\alpha]_D^{20}$ + 90.8° (C = 1 in CHCl$_3$). IR (Nujol) 1700, 1680 cm$^1$ (C = O).

EXAMPLE 2

To a suspension of 70% sodium hydrosulfide (technical grade) (7.5 g) in N,N-dimethylacetamide (120 ml), n-butyl isothiocyanate (11.8 g) is added. The mixture is stirred at room temperature for about 30 minutes and dried over anhydrous magnesium sulfate (18.0 g) while stirring for 6 hours. After removal of the magnesium sulfate by filtration, cis-1,3-dibenzylhexahydrofuro[3,4-d]imidazole-2,4-dione (10.0 g) is added to the filtrate, and the mixture is heated with stirring at 110°C for 6 hours. By the same workup of the reaction as in Example 1, cis-1,3-dibenzylhexahydrothieno[3,4-d]imidazole-2,4-dione (8.98 g) is obtained. Yield, 85.5%. M.P. 122 to 123°C. $[\alpha]_D^{20}$ + 91.0° (C = 1 in CHCl$_3$).

EXAMPLE 3

To a suspension of 70% sodium hydrosulfide (technical grade) (7.5 g) in N,N-dimethylacetamide (120 ml), isobutyl isothiocyanate (11.8 g) is added. The mixture is stirred at room temperature for about 30 minutes and dried over anhydrous magnesium sulfate (18.0 g) while stirring for 6 hours. After removal of the magnesium sulfate by filtration, cis-1,3-dibenzylhexahydrofuro[3,4-d]imidazole-2,4-dione (10.0 g) is added to the filtrate, and the mixture is heated with stirring at 110°C for 6 hours. By the same workup of the reaction as in Example 1, cis-1,3-dibenzylhexahydrothieno[3,4-d]imidazole-2,4-dione (9.20 g) is obtained. Yield, 88.0%. M.P. 121° to 122.5°C $[\alpha]_D^{20}$ + 89.8° (C = 1 in CHCl$_3$).

EXAMPLE 4

Ethyl isothiocyanate (9.7 g) is added to a suspension of 70% sodium hydrosulfide (technical grade) (7.5 g) in N,N-dimethylacetamide (120 ml). The mixture is stirred at room temperature for about 30 minutes and dried over molecular sieves (type 4A) (28.0 g) while stirring for 6 hours. After removal of the molecular sieves by filtration, cis-1,3-dibenzylhexahydrofuro[3,4-d]imidazole-2,4-dione (10.0 g) is added to the filtrate, and the mixture is heated with stirring at 110°C for 6 hours. By the same workup of the reaction as in Example 1, cis-1,3-dibenzylhexahydrothieno[3,4-d]imidazole-2,4-dione (8.45 g) is obtained. Yield, 80.5%. M.P. 122° to 123°C $[\alpha]_D^{20}$ + 90.5° (C = 1 in CHCl$_3$).

EXAMPLE 5

To a suspension of 70% sodium hydrosulfide (technical grade) (7.5 g) in N,N-dimethylacetamide (120 ml), cyclohexyl isothiocyanate (7.7 g) is added. The mixture is stirred at room temperature for about 30 minutes and dried over anhydrous magnesium sulfate (18.0 g) while stirring for 6 hours. After removal of the magnesium sulfate by filtration, cis-1,3-dibenzylhexahydrofuro[3,4-d]imidazole-2,4-dione (10.0 g) is added to the filtrate, and the mixture is heated with stirring at 120°C for 6 hours. By the same workup of the reaction as in Example 1, cis-1,3-dibenzylhexahydrothieno[3,4-d]imidazole-2,4-dione (8.39 g) is obtained. Yield, 80.0%. M.P. 122° to 123°C. $[\alpha]_D^{20}$ + 90.5° (C = 1 in CHCl$_3$).

EXAMPLE 6

Phenyl isothiocyanate (13.8 g) is added to a suspension of 70% sodium hydrosulfide (technical grade) (7.5 g) in N,N-dimethylacetamide (120 ml). The mixture is stirred at room temperature for about 30 minutes and dried over anhydrous magnesium sulfate (18.0 g) while stirring for 6 hours. After removal of the magnesium sulfate by filtration, cis-1,3-dibenzylhexahydrofuro[3,4-d]imidazole-2,4-dione (10.0 g) is added to the filtrate, and the mixture is heated with stirring at 120°C for 6 hours. By the same workup of the reaction as in Example 1 and moreover recrystallization of the product twice from aqueous methanol, cis-1,3-dibenzylhexahydrothieno[3,4-d]imidazole-2,4-dione (8.08 g) is obtained. Yield, 77.0%. M.P. 126° to 127°C.

EXAMPLE 7

To a suspension of 70% sodium hydrosulfide (technical grade) (7.5 g) in sulfolane (120 ml), n-butyl isothiocyanate (11.8 g) is added. The mixture is stirred at room temperature for about 30 minutes and dried over anhydrous magnesium sulfate (18.0 g) while stirring for 6 hours. After removal of the magnesium sulfate by filtration, cis-1,3-dibenzylhexahydrofuro[3,4-d]imidazole-2,4-dione (10.0 g) is added to the filtrate, and the mixture is heated with stirring at 120°C for 4 hours. By the same workup of the reaction as in Example 1, cis-1,3-dibenzylhexahydrothieno[3,4-d]imidazole-2,4-dione (8.99 g) is obtained. Yield, 86.0%. M.P. 122° to 123°C. $[\alpha]_D^{20} + 90.6°$ (C = 1 in $CHCl_3$).

What is claimed is:

1. A process for the conversion of a hexahydrofuro[3,4-d]imidazole-2,4-dione compound having the formula:

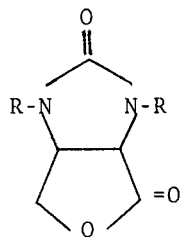

wherein R is alkyl, aryl or aralkyl into the corresponding hexahydrothieno[3,4-d]imidazole-2,4-dione compound having the formula:

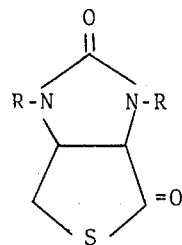

wherein R is as defined above which comprises reacting the starting hexahydrofuro[3,4-d]imidazole-2,4-dione compound with a dithiocarbamate having the formula R'NHCSSM wherein R' is alkyl, cycloalkyl or aryl and M is an alkali metal.

2. The process according to claim 1, wherein the reaction is effected in a high boiling point polar solvent.

3. The process according to claim 2, wherein the high boiling point polar solvent is sulfolane, N,N-dimethylformamide, N,N-dimethylacetamide, tetramethylurea or hexamethylphosphoramide.

4. The process according to claim 1, wherein the reaction is effected at a temperature of about 100° to 120°C.

5. The process according to claim 1, wherein the reaction is effected for about 4 to 6 hours.

6. The process according to claim 1, wherein the dithiocarbamate is prepared by reacting an alkali metal hydrosulfide with an isothiocyanate.

7. The process according to claim 6 wherein the isothiocyanate is an alkyl isothiocyanate, a cycloalkyl isothiocyanate or an aryl isothiocyanate.

8. The process according to claim 6, wherein the dithiocarbamate is subjected to the reaction with the hexahydrofuro[3,4-d]imidazole-2,4-dione compound after its separation from the reaction mixture for preparing the same.

9. The process according to claim 6, wherein the dithiocarbamate is subjected to the reaction with the hexahydrofuro[3,4-d]imidazole-2,4-dione compound without its separation from the reaction mixture for preparing the same.

* * * * *